United States Patent [19]

Lerch

[11] Patent Number: 4,635,484
[45] Date of Patent: Jan. 13, 1987

[54] ULTRASONIC TRANSDUCER SYSTEM

[75] Inventor: Reinhard Lerch, Erlangen, Fed. Rep. of Germany

[73] Assignee: Siemens Aktiengesellschaft, Berlin and Munich, Fed. Rep. of Germany

[21] Appl. No.: 742,157

[22] Filed: Jun. 6, 1985

[30] Foreign Application Priority Data

Jun. 14, 1984 [DE] Fed. Rep. of Germany ....... 3422115

[51] Int. Cl.$^4$ ............................................. G01N 29/00
[52] U.S. Cl. ...................................... 73/628; 310/336; 128/660; 73/625
[58] Field of Search ................. 73/628, 624, 625, 626, 73/632, 644; 310/334, 335, 336, 800; 128/660

[56] References Cited

U.S. PATENT DOCUMENTS

| | | | |
|---|---|---|---|
| 3,457,543 | 7/1969 | Akervold et al. | 367/155 |
| 3,924,454 | 12/1975 | McElroy et al. | 73/628 |
| 4,011,750 | 3/1977 | Robinson | 73/628 |
| 4,366,406 | 12/1982 | Smith et al. | 310/334 |
| 4,398,421 | 8/1983 | White | 73/628 |
| 4,446,395 | 5/1984 | Hadjicostis | 310/334 |
| 4,459,853 | 7/1984 | Miwa et al. | 73/626 |
| 4,537,074 | 8/1985 | Dietz | 73/628 |
| 4,569,231 | 2/1986 | Carnes et al. | 73/626 |

FOREIGN PATENT DOCUMENTS 3014878 10/1981 Fed. Rep. of Germany .
1505411 3/1978 United Kingdom .

OTHER PUBLICATIONS

"Design Procedure for Producing Desired Beamwidths", by S. Means, Navy Technical Disclosure Bulletin, vol. 2, No. 8, Aug. 1977, pp. 47 to 51.
"Experimentelle Untersuchungen zum Aufbau von Ultraschallbreitbandwandlern", by Richter et al., Biomedizinische Technik, vol. 27, 1982.

*Primary Examiner*—Stephen A. Kreitman
*Attorney, Agent, or Firm*—Thomas H. Jackson

[57] ABSTRACT

An ultrasonic transducer system is disclosed consisting of a support body (2), a radiating layer (8,9), a first $\lambda/4$ matching layer (10,11) and a second $\lambda/4$ matching layer (12,13). According to the invention, at least two ultrasonic transducers (4,6) with different and predetermined mid-frequencies are attached to a common support body (2) and have natural foci which overlap if the ultrasonic transducers (4,6) are mechanically separated. The ultrasonic transducer (4), having the higher mid-frequency, is provided with a larger radiating surface (4). This configuration, through the appropriate selection of the mid-frequencies, allows compensation for the frequency dependent damping of the transmission medium by frequency related weighting during radiation. In this manner, substantial improvements with respect to bandwidth of the total transmission path, from transmitting transducer through transmission media to receiving transducer, and the image quality can be realized.

6 Claims, 7 Drawing Figures

ULTRASONIC TRANSDUCER SYSTEM

BACKGROUND OF THE INVENTION

1. Technical Field

This invention relates to the field of ultrasonic transducer systems generally and, in particular, to one in which a number of ultrasonic transducers are attached to a common support body.

2. Description of the Prior Art

Broad band ultrasonic transducers are employed in medical ultrasonic diagnostics and in the non-destructive testing of materials. Particularly in medical applications, where the losses in the coupling between tissue and a sonic transducer must be kept to a minimum, there is a need to improve the electro-mechanical and acoustic characteristics of these transducer systems.

An ultrasonic transducer is known where its ceramic transducer is coupled to a load medium, for example, tissue or water, through two $\lambda/4$ (quarter wave) matching layers. This transducer system consists of a backing of epoxy resin having an acoustic impedance of $3 \times 10^6$ Pas/m, a ceramic transducer, a first $\lambda/4$ matching layer of glass with an acoustic impedance of $10 \times 10^6$ Pas/m and a second $\lambda/4$ matching layer of polyacrylate or of epoxy resin with an acoustic impedance of $3 \times 10^6$ Pas/m. The ceramic transducer is attached to a backing. The attachment of the glass plate as the first $\lambda/4$ matching layer is accomplished with an adhesive cement of very low viscosity, so that the thickness of the adhesive cement is in the order of 2 um. The epoxy resin as the second $\lambda/4$ matching layer is poured directly over the first $\lambda/4$ matching layer. Through these double $\lambda/4$ matching layers, one only obtains an improvement in the bandwidth of the ceramic radiating layer. The bandwidth of this ultrasonic transducer is about 60 to 70% of the mid-frequency. (Experimental Investigation of Ultrasonic Transducers—Biomedical Technology—volume 27, issue 7 to 8, 1982, pages 182 to 185).

Another ultrasonic transducer has been proposed having a radiating layer made of a material with a comparatively high dielectric constant and high acoustic impedance and which employs two $\lambda/4$ matching layers. The first $\lambda/4$ matching layer which faces the radiating layer has an acoustic impedance of about $14 \times 10^6$ Pas/m and is made, for example, from porcelain or a glass-like material (macor), preferably of quartz glass. The second 80 /4 matching layer which is facing the load has an acoustic impedance of about $4 \times 10^6$ Pas/m and is made, for example, from polyvinylchloride PVC or, more particularly, from polyvinylidine flouride PVDF, and can also be employed as a receiving layer. In addition, the first $\lambda/4$ matching layer is used as a backing for the receiving layer. Through this configuration an ultrasonic transducer is obtained having a radiating layer that may be coupled to a load with minimum reflection and broad bandwidth and which has a receiving layer of unusual sensitivity and bandwidth. (German patent application No. P33 09 236.2).

SUMMARY OF THE INVENTION

In these known ultrasonic transducers, the bandwidth and coupling of the ultrasonic transducer was improved only for a predetermined load. The present invention, however, is based on the recognition that in ultrasonic systems used in examining objects with frequency dependent damping, the transmission characteristics of the medium to be examined must be taken into consideration.

The invention then basically seeks to define an ultrasonic transducer system in which the total transmission path, from the transmitting transducer through the transmission media to the receiving transducer, has been substantially improved with regard to the bandwidth and the image quality and, in particular, in which the frequency range of the coupling medium is frequency compensated.

In accordance with the present invention, this problem is solved by providing first and second or more transducers having different mid-frequencies attached to a common support body. An ultrasonic transducer system with such a plurality of ultrasonic transducers of different and varied predetermined mid-frequencies and overlapping natural foci are physically separated from each other by an air column. Also, the radiating surface of the ultrasonic transducer having the highest mid-frequency is substantially larger than that of the other ultrasonic transducers. Through this configuration a substantial improvement in the bandwidth of the overall transmission path, from transmitting transducer through transmission media to receiving transducer, is obtained, resulting in an improved image quality. Also, on the basis of the selected mid-frequency, the frequency dependent damping of the coupling medium may be compensated by frequency-related weighting during radiation. That is, the bandwidth of the transmitting transducer remains at least approximately constant and its mid-frequency need not be shifted toward the lower frequencies as a function of the transmission path.

In a preferred embodiment of the ultrasonic transducer system, one of the ultrasonic transducers is divided into a number of sub-resonators connected electrically in parallel. As a result, a nearly unlimited selection in the arrangement of the radiating surfaces of the ultrasonic transducers is possible and the sub-resonators may be assembled into virtually any configuration constituting an ultrasonic transducer system.

In a particularly advantageous embodiment, the second $\lambda/4$ matching layer of the ultrasonic transducer having the highest mid-frequency is also employed as the receiving layer. The second $\lambda/4$ matching layer is composed of a piezoelectric plastic, for example, polyvinyl chloride PVC, or more particularly, polyvinylidine fluoride PVDF. Through this type of configuration, a broad band ultrasonic transducer is obtained, which can be employed in connection with pulse-echo transmission and detection methods.

By way of further explanations, reference is made to the figures showing an embodiment of an ultrasonic transducer in accordance with the invention.

DETAILED DESCRIPTION

Figure 1:
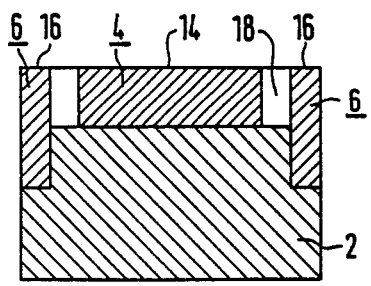
FIG. 1 shows a sectional view through a cylindrically shaped ultrasonic transducer system in accordance with the present invention.
Figure 2:
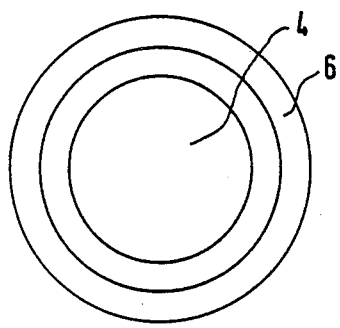
FIG. 2 is a top view of the ultrasonic transducer of FIG. 1.

In the embodiment shown in FIGS. 1 and 2, an ultrasonic transducer system is shown comprised of a support body and two ultrasonic transducers 4 and 6 mounted in common to the support body 2. The ultrasonic transducer 4, may be, for example, provided in the form of a cylinder, while ultrasonic transducer 6 may be provided as a hollow cylinder. The hollow cylinder ultrasonic transducer 6 surrounds the cylindrical ultrasonic transducer 4 in a manner ensuring that the radiating surfaces 14 and 16 are arranged in one plane and the natural foci of ultrasonic transducers 4 and 6 are superposed. In addition, the ultrasonic transducers 4 and 6 are separated acoustically, e.g. by means of an air column 18 or by a material of high mechanical damping. The ultrasonic transducers are furthermore separately electrically driven. The respective mid-frequency selected for the ultrasonic transducers 4 and 6, may be 4 MHz for the cylindrically-shaped ultrasonic transducer 4 and 2 MHz for the hollow cylindrically-shaped ultrasonic transducer 6. For these two mid-frequencies the difference in tissue damping is approx. 21 dB for a transmission path of e.g. 15 cm and a tissue damping factor of e.g. 0.7 dB/MHz×cm. This corresponds to a ratio of the acoustic output powers of the ultrasonic transducers 4 and 6 of approx. 1:130.

As known, the delivered power $P_s$ of an ultrasonic element vibrating in its thickness mode is proportional to the product of the radiating surface area A, the square of the frequency $f^2$ and the square of the transmission voltage $V^2$. The mid frequencies of the two ultrasonic transducers 4 and 6 are in the ratio of 2:1, the ultrasonic transducer 4 of the higher mid-frequency is provided with a larger radiating surface area 14 than the ultrasonic transducer 6. The ratio of the radiating surfaces 14 and 16, is e.g. 5:1. As a result, the mechanical radiated power output of the ultrasonic transducer 4 is already higher by a factor of 20 than that of the ultrasonic transducer 6.

If the ultrasonic transducer system is to be used in the transmitting mode, a PDVF element vibrating in its thickness mode is preferred whose mid-frequency may, for example, be so selected that the higher frequency band (approx. 4 MHz in the exemplified embodiment) may be raised by a factor of 2 to 3 due to the resonance of the receiver. Should the difference in power output between the two mid-frequencies continue, compensation is possible by increasing the transmitting voltage V of the ultrasonic transducer 4. It is furthermore possible to compensate remaining differences in the power output by adjusting the gains of the receiver amplifiers.

It follows therefore that in the design of an ultrasonic diagnostic device with the present ultrasonic transducer system together with a broad banded ultrasonic receiving mode, the selection of the mid-frequencies and the size of the radiating surface areas must be based on (1) the geometry of the ultrasonic transducers used in the ultrasonic transducer system, (2) the dampening effect of the transmission medium as a function of the transmission path traveling through same as well as (3) the minimum requirements of the broad banded ultrasonic signal to be received. On the basis of the frequency dependent compensation achieved as a result of the wider bandwidth, both resolution and image quality are improved.

Figure 3:
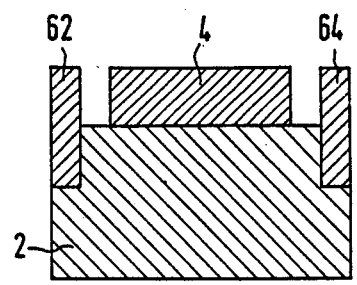
FIG. 3 shows an additional box-shaped advantageous embodiment of the ultrasonic transducer system in a sectional view.
Figure 4:
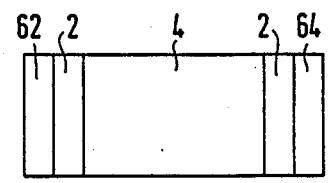
FIGS. 4 and 5 show two different embodiments of the system of FIG. 3 in top view.

In another preferred embodiment shown in FIGS. 3 and 4, one of the ultrasonic transducers 4 and 6, e.g. the ultrasonic transducer with the lower mid-frequency, is divided into two sub-resonators 62 and 64 connected electrically in parallel and which are arranged with one of the other ultrasonic transducers 4 or 6 on a common support body.

Figure 5:
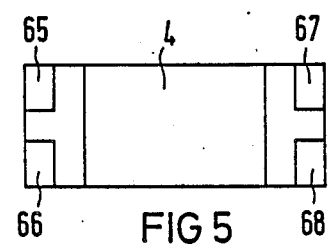

In a preferred embodiment shown in FIG. 5, the ultrasonic transducer 6 is divided into more than two, e.g. into four sub-resonators 65, 66, 67, and 68, connected electrically in parallel and which surround the ultrasonic transducer 4. Though this configuration, it becomes possible for the natural foci to overlap despite the high ratio between the radiating surface area of the ultrasonic transducer 4 and the sum of the radiating surface areas of the ultrasonic transducers 65, 66, 67, and 68.

Figure 6:
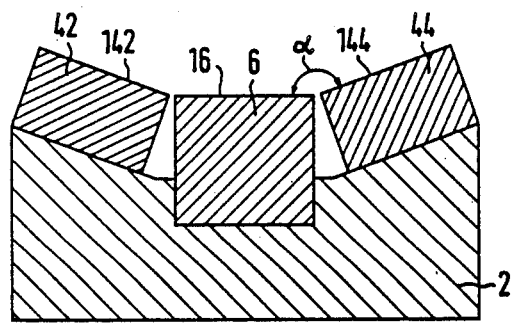
FIG. 6 shows an additional advantageous embodiment of the ultrasonic transducer system in a sectional view.
Figure 7:
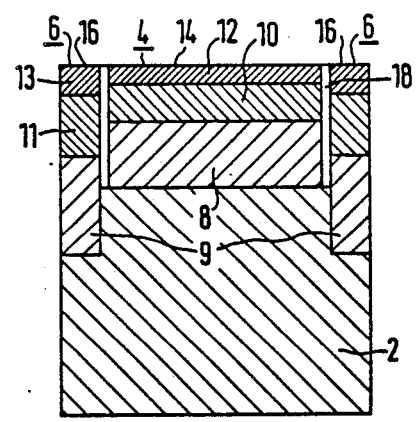
FIG. 7 shows a particularly advantageous embodiment of the present ultrasonic transducer system in sectional view.

Referring briefly to both FIG. 6 and FIG. 7, it is obvious that the sectional views depicted may be either cylindrical or box-shaped. In the further advantageous embodiment, shown in FIG. 6, the ultrasonic transducer 4 of the higher mid-frequency is, for example, divided into two sub-resonators 42 and 44 connected electrically in parallel. The radiating surface areas 142 and/or 144 of these sub-resonators each form an angle with the radiating surface area 16 of the ultrasonic transducer 6. The sub-resonators 42 and 44 and the ultrasonic transducer 6 are attached to a common support body 2. In this arrangement there is an improvement in the spatial superposition of the sonic fields of the ultrasonic transducers 4 and 6.

In an especially advantageous embodiment shown in FIG. 7, the ultrasonic transducers 4 and 6 show a transmitting layer 8 and/or 9 and two λ/4 matching layers each, respectively 10 and/or 11, or 12 and/or 13. The transmitting layer 8 and/or 9 is coupled at its load facing radiation surface, the load being, for example, biological tissue, to the first λ/4 matching layer 10 and/or 11. The second λ/4 matching layer 12 and/or 13 is located between the load and the first λ/4 matching layer 10 and/or 11 to which it is attached. A material of relatively high dielectric constant and high acoustic impedance, for example, piezo-ceramic material, may be used as transmitting layers 8 and 9. In this particular case, the transmitting layer may comprise lead zirconate-titanate PbZrTi or lead meta niobate Pb(NbO$_3$).

For the first λ/4 matching layers 10 and 11 having an impedance of, for example, 14×10$^6$ Pas/m, material such as porcelain, preferably quartz glass, in particular, a glass-like material (macor) can be used. For the second λ/4 matching layers 12 and 13, to achieve an impedance of, for example, approximately 4×10$^6$ Pas/m, material such as polyvinyl chloride PVC or more particularly polyvinylidine fluoride PVDF can be used.

One of the two λ/4 matching layers 12 and 13 of the ultrasonic transducers 4 and 6 may be adapted to service simultaneously as the receiving layer. Preferably the second λ/4 matching layer 12 of the ultrasonic transducer 4 of the higher mid-frequency is employed as the receiving layer. In order for the second λ/4 matching layer to simultaneously serve as the receiving layer, the polyvinylidine fluoride PVDF must be polarized and equipped with electrical connections (not shown). On the basis of this configuration, a broad band ultrasonic transducer system is obtained which compensates for frequency dependent damping in, for example, biological tissue. As a result, an optimal broad band signal with a constant spectrum over a wide frequency range is obtained.

What is claimed is:

1. An ultrasonic transducer system characterized by at least two ultrasonic transducers (4,6) having different predetermined mid-frequencies, attached to a common support body and having overlapping natural foci, the ultrasonic transducers (4,6) being separately, electrically controllable, the ultrasonic transducer (4) having the highest mid-frequency being equipped with the largest radiating surface area for producing the highest acoustic power output.

2. An ultrasonic transducer system according to claim 1, characterized by one of the, at least, two ultrasonic transducers (4,6) being arranged to form a number of sub-resonators connected in parallel electrically.

3. An ultrasonic transducer system according to claim 1 characterized by arranging the radiating surfaces (14,16) of the ultrasonic transducers (4,6) in a plane.

4. An ultrasonic transducer system according to claim 1 characterized by the radiating surfaces (142,144,16) of the, at least, two ultrasonic transducers (42,44 and/or 6) being inclined toward one another.

5. An ultrasonic transducer system according to claim 1 characterized by the ultrasonic transducers (4,6) being provided with a radiating surface (8 and/or 9) of a material having a relatively high dielectric constant and a high acoustic impedance, the surface being coupled on its side facing a load to a first $\lambda/4$ matching layer (10 and/or 11), the first $\lambda/4$ matching layer attached respectively to a second $\lambda/4$ matching layer (12 and/or 13), the second layer being located beween the first $\lambda/4$ matching layer (10 and/or 11) and the load.

6. An ultrasonic transducer system according to claim 5 characterized by at least one of the second $\lambda/4$ matching layers (12 and/or 13) of the ultrasonic transducer (4 and/or 60) being employed as a receiving layer and comprising piezo-electrical plastic.

* * * * *